US012797550B2

(12) United States Patent
Boström

(10) Patent No.: US 12,797,550 B2
(45) Date of Patent: Nov. 17, 2026

(54) SIMPLE MEDICAMENT DELIVERY DEVICE

(71) Applicant: SHL MEDICAL AG, Zug (CH)

(72) Inventor: Anders Boström, Ingaro (SE)

(73) Assignee: SHL Medical AG, Zug (CH)

( * ) Notice: Subject to any disclaimer, the term of this patent is extended or adjusted under 35 U.S.C. 154(b) by 757 days.

(21) Appl. No.: 18/267,219

(22) PCT Filed: Dec. 9, 2021

(86) PCT No.: PCT/EP2021/084906
§ 371 (c)(1),
(2) Date: Jun. 14, 2023

(87) PCT Pub. No.: WO2022/135946
PCT Pub. Date: Jun. 30, 2022

(65) Prior Publication Data

US 2024/0058541 A1 Feb. 22, 2024

(30) Foreign Application Priority Data

Dec. 22, 2020 (EP) .................................... 20216380

(51) Int. Cl.
*A61M 5/24* (2006.01)
*A61M 5/20* (2006.01)
*A61M 5/32* (2006.01)

(52) U.S. Cl.
CPC ............ *A61M 5/2425* (2013.01); *A61M 5/20* (2013.01); *A61M 5/3202* (2013.01); *A61M 2005/2073* (2013.01)

(58) Field of Classification Search
CPC .... A61M 2005/208; A61M 2005/2073; A61M 2005/3267; A61M 5/2425; A61M 5/20; A61M 5/3202; A61M 5/2033; A61M 5/24; A61M 5/2422; A61M 5/3153; A61M 5/31535; A61M 5/31566; A61M 5/31565;
(Continued)

(56) References Cited

U.S. PATENT DOCUMENTS 3,605,744 A 9/1971 Dwyer
10,232,117 B2 3/2019 Halseth
(Continued)

FOREIGN PATENT DOCUMENTS

CN 102665805 A 9/2012
CN 103328026 A 9/2013
(Continued)

OTHER PUBLICATIONS

International Search Report and Written Opinion for Int. App. No. PCT/EP2021/084906, mailed Jan. 24, 20222.

*Primary Examiner* — Kevin C Sirmons
*Assistant Examiner* — Alexandra Lalonde
(74) *Attorney, Agent, or Firm* — McDonnell Boehnen Hulbert & Berghoff LLP

(57) ABSTRACT

The present disclosure provides a medicament delivery device having a front assembly, a rear assembly, and a bayonet connection configured to attach the front assembly and the rear assembly. The front assembly has a front body and a syringe holder arranged in the front body. The rear assembly has a rear body provided with a plunger rod. The front body is configured to move axially relative to the rear body to enable the plunger rod to move forward inside the syringe holder.

16 Claims, 8 Drawing Sheets

(58) Field of Classification Search
CPC ............ A61M 5/31571; A61M 5/3271; A61M 5/3272; A61M 5/3243; A61M 5/3204; A61M 5/2429; A61M 5/283; A61M 2005/2403; A61M 2005/2407; A61M 2005/2418; A61M 2005/2488
See application file for complete search history.

(56) References Cited

U.S. PATENT DOCUMENTS

| | | | | |
|---|---|---|---|---|
| 12,343,505 | B1 * | 7/2025 | Hee-Hanson | A61M 5/31501 |
| 2011/0202011 | A1 * | 8/2011 | Wozencroft | A61M 5/31505 604/192 |
| 2011/0306936 | A1 | 12/2011 | Holmqvist | |
| 2012/0010576 | A1 | 1/2012 | Raab et al. | |
| 2013/0267897 | A1 | 10/2013 | Kemp et al. | |
| 2015/0374927 | A1 * | 12/2015 | Dasbach | A61M 5/3202 604/192 |
| 2016/0175528 | A1 | 6/2016 | Marshall et al. | |
| 2019/0209785 | A1 * | 7/2019 | Roberts | A61M 5/3245 |
| 2019/0321561 | A1 | 10/2019 | Montgomery et al. | |
| 2020/0054838 | A1 | 2/2020 | Olson et al. | |

FOREIGN PATENT DOCUMENTS

| | | | |
|---|---|---|---|
| EP | 1443992 | B1 | 1/2007 |
| EP | 1919541 | B1 | 8/2016 |
| EP | 2488237 | B1 | 7/2018 |
| EP | 3235530 | B1 | 1/2020 |
| JP | 2014-079375 | A | 5/2014 |
| TW | 201433326 | A | 9/2014 |
| WO | 2012/000833 | A1 | 1/2012 |
| WO | 2012/003516 | A2 | 1/2012 |
| WO | 2012/093069 | A1 | 7/2012 |
| WO | 2013/016832 | A1 | 2/2013 |
| WO | 2014/095424 | A1 | 6/2014 |
| WO | 2015/062915 | A1 | 5/2015 |
| WO | 2015/113969 | A1 | 8/2015 |
| WO | 2015/121081 | A1 | 8/2015 |
| WO | 2018/065714 | A1 | 4/2018 |
| WO | 2020/043495 | A1 | 3/2020 |

* cited by examiner

SIMPLE MEDICAMENT DELIVERY DEVICE

CROSS REFERENCE TO RELATED APPLICATIONS

The present application is a U.S. National Phase application pursuant to 35 U.S.C. § 371 of International Application No. PCT/EP2021/084906 filed Dec. 9, 2021, which claims priority to European Patent Application No. 20216380.4 filed Dec. 22, 2020. The entire disclosure contents of these applications are herewith incorporated by reference into the present application.

TECHNICAL FIELD

The present disclosure generally relates to medicament delivery devices.

BACKGROUND

Medicament delivery devices such as injectors are nowadays often handled by the end user during medicament delivery.

Some medicament delivery devices contain a syringe. Syringes are used for a single medicament delivery operation.

In some cases, the entire medicament delivery device may be disposable so that a user only has to be concerned about the medicament delivery operation and the disposal of the medicament delivery device.

In other cases, the medicament delivery device may be configured to be used multiple times. This requires changing of the syringe. Such an operation may be relatively complex, especially if the user has a functional impairment.

SUMMARY

It would be desirable to provide a multi-use medicament delivery device for syringes, which is simple to handle for the user.

An object of the present disclosure is to provide a medicament delivery device which solves, or at least mitigates problems of the prior art.

There is hence provided a medicament delivery device comprising: a front assembly, and a rear assembly configured to be attached to the front assembly, wherein the front assembly has a front body and a syringe holder arranged in the front body, wherein the rear assembly has a rear body provided with a plunger rod, wherein the front body is configured to move axially relative to the rear body to enable the plunger rod to move forward inside the syringe holder, wherein the front assembly and the rear assembly are configured to be attached by means of a bayonet connection.

A medicament delivery device which is simple to assembly when loading with a syringe and to disassemble when removing a used syringe can thereby be provided. The bayonet connection ensures simple handling for connecting and disconnecting the front assembly and the rear assembly before and after use of the medicament delivery device.

With “rearwards” and “rearward direction” as used herein is meant an axial direction from the front body towards the rear body. With “forward” and “forward direction” is meant an axial direction from the rear body towards the front body.

According to one embodiment the front body has a radial pin forming one part of the bayonet connection and the rear body has a bayonet slot forming another part of the bayonet connection, and wherein the pin is configured to run in the bayonet slot.

According to one embodiment the bayonet slot transitions into an axial slot extending rearwards along the rear body, wherein the pin is configured to run in the axial slot to enable axial movement of the front body relative to the rear body when the front body and the rear body are locked by the bayonet connection.

According to one embodiment the axial length of the axial slot defines a stroke length of the front body. The stroke length is the amount that the front body is configured to be moved axially relative to the rear body to perform medicament delivery.

According to one embodiment the pin is provided on an outer surface of the front body and the bayonet slot extends radially through the rear body.

One embodiment comprises an outer rear body configured to receive the rear body and a rear part of the front body, wherein the outer rear body has an axial rib provided on its inner surface, the axial rib being configured to restrict movement of the pin in the bayonet slot to maintain the front body and the rear body in a locked state.

According to one embodiment the outer rear body has a front flange provided with a radial opening aligned with the mouth of the bayonet slot, the radial opening being configured to receive the pin when the front assembly and rear assembly are assembled or disassembled with each other. The radial opening acts as a guide for the pin into the bayonet slot when the front assembly is being assembled with the rear assembly.

According to one embodiment the outer rear body has a release button which in a default position has a radially inwards extending structure configured to prevent axial movement of the pin rearwards in the axial slot, to thereby prevent the front body to move axially rearwards relative to the rear body, wherein the release button is configured move the radial structure radially outwards when the release button is depressed to enable the pin to run rearwards in the axial slot. Accidental expulsion of medicament may thereby be prevented.

According to one embodiment the release button has a seesaw-structure with one end being provided with the radially inwards extending structure.

According to one embodiment the rear body has an outer shell, and the plunger rod is arranged immovable relative to the outer shell, wherein the plunger rod extends in the forward direction inside the outer shell. The plunger rod is moved forward in the front body and the syringe holder by moving the front body rearwards in the rear body.

One embodiment comprises a front resilient member arranged in the front body and configured to bias the syringe holder towards a rear end of the front body.

One embodiment comprises an axially movable syringe stop arranged in the rear body concentrically with the plunger rod, wherein the syringe stop has radial protrusions and the rear body comprises axial slots in which the radial protrusions are configured to run to guide axial movement of the syringe stop, and a rear resilient member configured to bias the syringe stop towards a front end of the rear body.

According to one embodiment the syringe stop is configured to bear against a rear end of the syringe holder.

According to one embodiment the rear resilient member has a higher stiffness than the front resilient member. Thereby, the syringe holder is first moved forwards in the front body as the front body is moved further into the rear body before the syringe stop is moved rearwards and the plunger rod is moved further into the syringe holder and thus the syringe. The needle of the syringe is thus exposed through the front body before medicament is expelled through the needle.

According to one embodiment the front body is a needle cover.

One embodiment comprises a cap provided with a first connection structure, the cap being configured to be removably attached to the front body, wherein the front body comprises a second connection structure configured to mate with the first connection structure to retain the cap on the front body.

According to one embodiment the one of the first connection structure and the second connection structure is an opening and the other one of the first connection structure and the second connection structure is a radial protrusion. The radial protrusion may be a pin.

According to one embodiment the syringe holder has a rear flange provided with rearwards extending radially flexible arms, each provided with a radially inwards extending protrusion.

The radially inwards extending protrusions may be configured to bear against a rear side of a rear syringe flange of a syringe to retain the syringe in the syringe holder.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

The specific embodiments of the present concept will now be described, by way of example, with reference to the accompanying drawings, in which.

DETAILED DESCRIPTION

The present concept will now be described more fully hereinafter with reference to the accompanying drawings, in which exemplifying embodiments are shown. The present concept may, however, be embodied in many different forms and should not be construed as limited to the embodiments set forth herein; rather, these embodiments are provided by way of example so that this disclosure will be thorough and complete, and will fully convey the scope of the present concept to those skilled in the art. Like numbers refer to like elements throughout the description.

Figure 1:
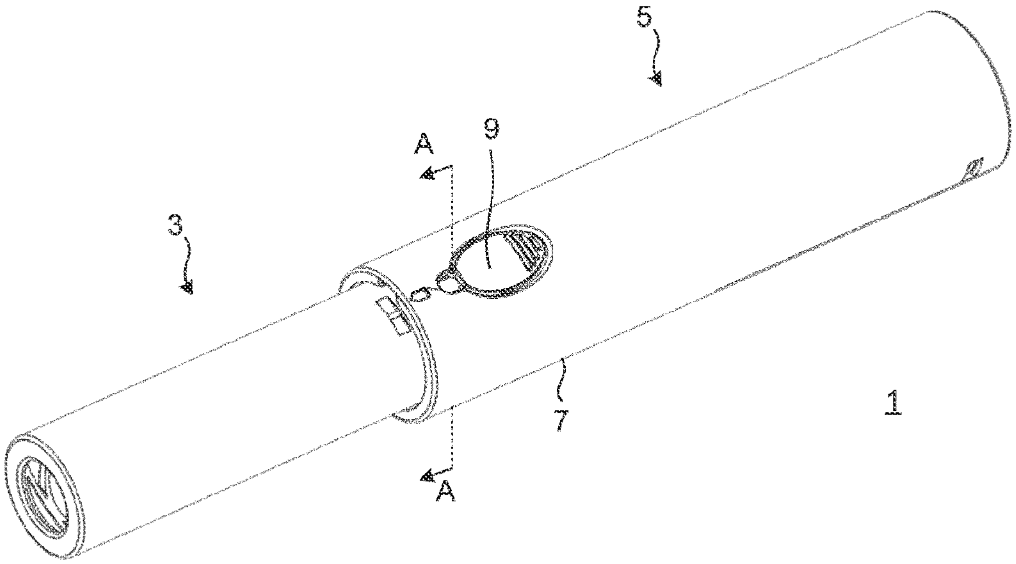
FIG. 1 is a perspective view of an example of a medicament delivery device.

FIG. 1 shows a perspective view of an example of a medicament delivery device 1. The exemplified medicament delivery device 1 is an injector. The injector in the present example is a manual injector.

The medicament delivery device 1 comprises a front assembly 3 and a rear assembly 5 configured to be releasably attached to the front assembly 3. The front assembly 3 and the rear assembly 5 are configured to be attached by means of a bayonet connection. The medicament delivery device 1 can thereby be loaded with a syringe, and a used syringe can be removed and replaced with a new syringe in a simple manner. The medicament delivery device 1 can thereby be reused multiple times.

The rear assembly 5 has an outer rear body 7 configured to receive the front assembly 3. The front assembly 3 is movable axially relative to the rear assembly 5. The front assembly 3 is configured to slide into the rear assembly 5 to perform medicament delivery.

The outer rear body 7 may be provided with a release button 9 which in a default position prevents the front assembly 3 from moving further into the outer rear body 7 for performing medicament delivery.

The release button can be depressed to release the front assembly 3 from being prevented to move axially further into the outer rear body 7 and enable the front assembly 3 to move axially further into the outer rear body 7 to perform medicament delivery.

Figure 2:
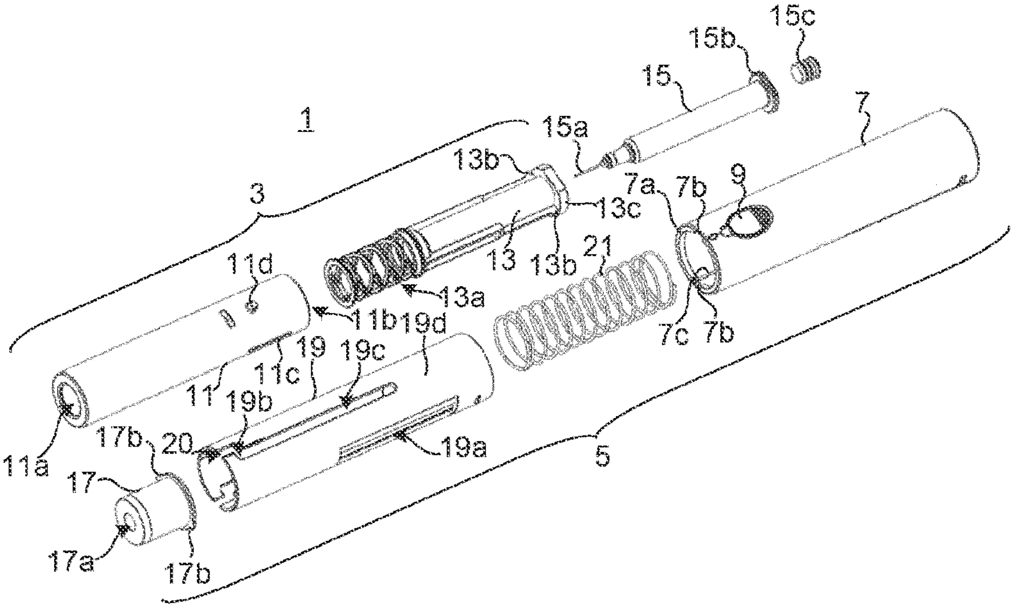
FIG. 2 depicts an exploded view of the medicament delivery device in FIG. 1.

FIG. 2 is an exploded view of the medicament delivery device 1. The front assembly 3 comprises a front body 11. The front body 11 is elongated and may have a generally tubular structure. The front body 11 is hollow and provided with a front opening 11*a* and a rear opening 11*b*. The front body 11 has axial slots 11*c*, of which one can be seen in FIG. 2.

The front body 11 is provided with a radial pin 11*d* which forms one part of the bayonet connection with the rear assembly 5. The pin 11*d* is provided on an outer surface of the front body 11. The pin 11*d* is provided on the rear half of the front body 11, for example on the rearmost one third or one fourth of the front body 11.

The front assembly 3 comprises a syringe holder 13. The front body 11 is configured to receive the syringe holder 13. The syringe holder 13 is configured to move axially relative to the front body 11.

The syringe holder 13 is configured to receive a syringe 15 containing medicament. The syringe has a needle 15*a* pointing in the forward direction.

In the present example, the syringe holder 13 comprises a front resilient member 13*a* forming a front end of the syringe holder 13. The front resilient member 13*a* may be a spring. In the example, the front resilient member 13*a* is integral with the syringe holder 13. The front resilient member 13*a* may in this case for example be made of a polymer material. Alternatively, the medicament delivery device could comprise a front resilient member which is a separate component. In this case, the front resilient member could for example be a metal spring.

The front resilient member 13*a* is configured to bear against e.g. a front flange of the front body 11. The syringe holder 13 is thereby biased rearwards in the front body 11.

The syringe holder 13 has radially outwards extending wings 13*b* configured to run in a respective one of the axial slots 11*c* of the front body 11 to guide the axial movement of the syringe holder 13 relative to the front body 11. The syringe holder 13 and the front body 11 are thereby rotationally locked relative to each other.

The syringe holder 13 has a rear flange 13*c* configured to mate with a non-circular rear syringe flange 15*b* of the syringe 15. The syringe 15 is thereby rotationally locked relative to the syringe holder 13. The syringe 15 may be provided with a stopper 15*c* arranged inside the syringe 15.

The rear assembly 5 comprises a syringe stop 17. The syringe stop 17 has an axial through-opening 17*a*. The syringe stop 17 has radial protrusions 17*b* extending radially outwards.

The rear assembly 5 comprises a rear body 19. The rear body 19 has a generally tubular structure. The rear body 19 is configured to receive the syringe stop 17. The rear body 19 has axial slots 19*a* configured to receive a respective one of the radial protrusions 17*b*. The radial protrusions 17*b* are configured to run in the axial slots 19*a* when the syringe stop 17 is moved axially relative to the rear body 19. The syringe stop 17 is thereby rotationally locked relative to the rear body 19.

The rear body 19 comprises a bayonet slot 19*b*. The bayonet slot 19*b* forms another part of the bayonet connection between the front assembly 3 and the rear assembly 5. In particular, the pin 11*d* and the bayonet slot 19*b* form the bayonet connection. The pin 11*d* is configured to run in the bayonet slot 19*b*.

The bayonet slot 19*b* extends radially through the rear body 19. The bayonet slot 19*b* has a first axial portion which runs to a front axial end of the rear body 19. The bayonet slot 19*b* also has a circumferential portion. In the rearward direction, the first axial portion transitions into the circumferential portion which extends generally in the circumferential direction.

The rear body 19 has an axial slot 19*c*. The axial slot 19*c* extends radially trough the rear body 19. The bayonet slot 19*b* transitions into the axial slot 19*c*, which extends axially rearwards along the rear body 19. The circumferential portion transitions into the axial slot 19*c*. The bayonet slot 19*b* and the axial slot 19*c* form a continuous slot in the rear body 19.

The pin 11*d* is configured to run in the axial slot 19*c* when the front assembly 3 and the rear assembly 5 are locked to each other by means of the bayonet connection and the front assembly 3 is pushed into the rear assembly 5.

The release button 9 is configured to prevent the pin 11*d* to move from the bayonet slot 19*b* into the axial slot 19*c* when the release button 9 is in the default position.

The rear body 19 has an outer shell 19*d*. The rear body 19 has a plunger rod (not shown in FIG. 2) extending axially inside the outer shell 19. The plunger rod extends from a rear end of the outer shell 19*d* towards a front end of the outer shell 19*d*. The plunger rod is arranged immovable relative to the outer shell 19*d*. The plunger rod may for example be integral with the outer shell 19*d*.

The syringe stop 17 is configured to be arranged concentrically with and radially outside of the plunger rod. The through-opening 17*a* of the syringe stop 17 is configured to receive a portion of the plunger rod. The plunger rod thus extends through the syringe stop 17.

The rear assembly 5 comprises a rear resilient member 21. The rear resilient member 21 may for example be a spring. The rear resilient member 21 is configured to bias the syringe stop 17 in the forward direction. When the front assembly 3 and the rear assembly 5 are assembled with each other, the front end of the syringe stop 17 bears against the rear end of the rear syringe flange 15*b* and biases the syringe 15 and thus the syringe holder 13 in the forward direction. The syringe stop 17 may also bear against a rear end of the rear flange 13*c* of the syringe holder 13.

The outer rear body 7 forms a housing of the rear assembly 5. The outer rear body 7 is configured to receive the rear resilient member 21, the rear body 19 and the syringe stop 17.

The outer rear body 7 has a front flange 7*a*. The front flange 7*a* is provided with a radial opening 7*b* axially aligned with the mouth 20 of the bayonet slot 19*b*. In case there are several bayonet slots 19*b*, the front flange 7*a* may be provided with a corresponding number of radial openings 7*b*. The radial opening 7*b* is configured to receive the pin 11*d*.

The outer rear body 7 has an axial rib 7*c* extending offset from the radial opening 7*b* in the circumferential direction. The axial rib 7*c* is provided on the inner surface of the outer rear body 7 and configured to restrict movement of the pin 11*d* when the pin 11*d* is arranged in the bayonet slot 19*b*, in particular the circumferential portion thereof. The front assembly 3 and the rear assembly 5 are thereby maintained in a locked state by the bayonet connection.

Figure 3A:
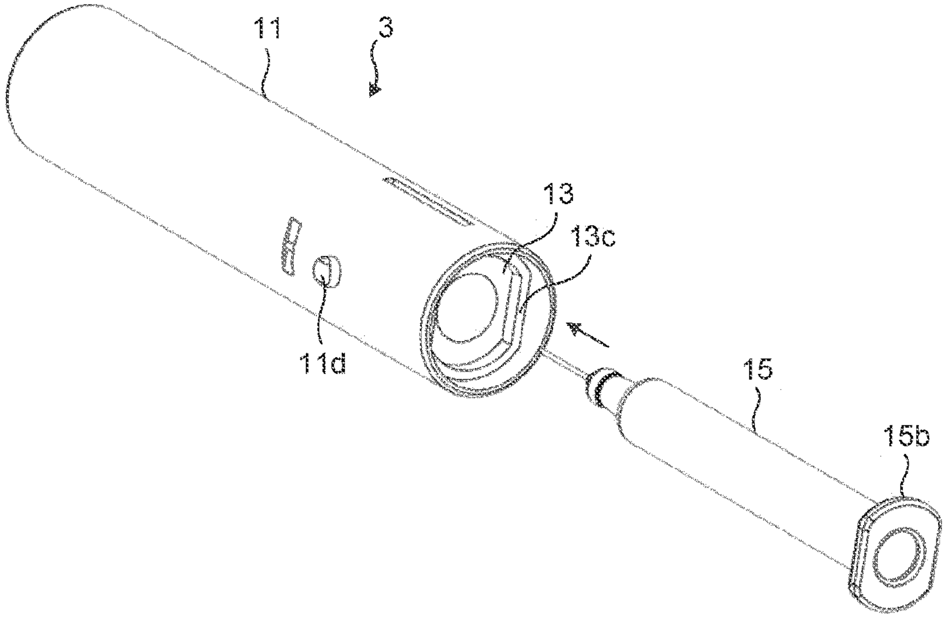
FIG. 3A is a perspective rear view of a front assembly prior to syringe insertion.

Turning now to FIG. 3*a*, the front assembly 3 is shown before the syringe 15 has been loaded into the syringe holder 13. The syringe 15 is brought into the syringe holder 13 from the rear end of the syringe holder 13.

Figure 3B:
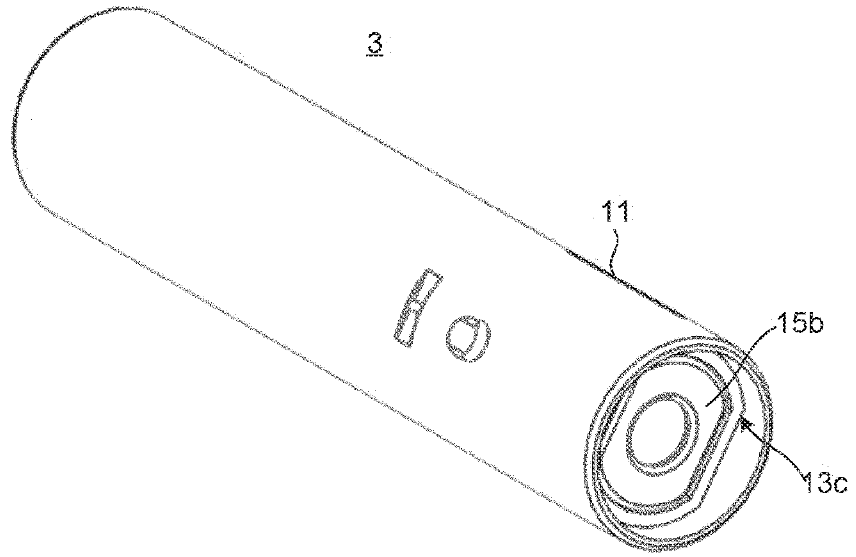
FIG. 3B is a perspective rear view of the front assembly in FIG. 3*a* after it has been loaded with a syringe.

FIG. 3*b* shows the front assembly 3 when the syringe holder 13 has been loaded with the syringe 15. Due to the non-circular shape of the rear syringe flange 15*b* and the corresponding shape of an opening in the rear flange 13*c* the rear syringe flange 15 mates with the rear syringe flange 15*b*. The syringe 15 is thus prevented from rotation relative to the syringe holder 13.

The loading of the syringe 15 into the front assembly 3 may advantageously be performed by the user.

Figure 4:
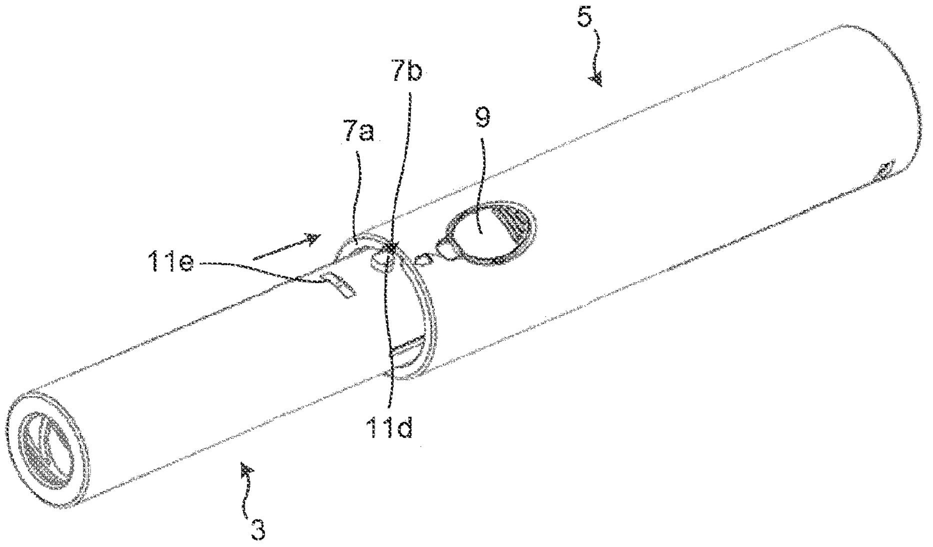
FIG. 4 is a perspective view of the medicament delivery device when the front assembly is assembled with the rear assembly.
Figure 5:
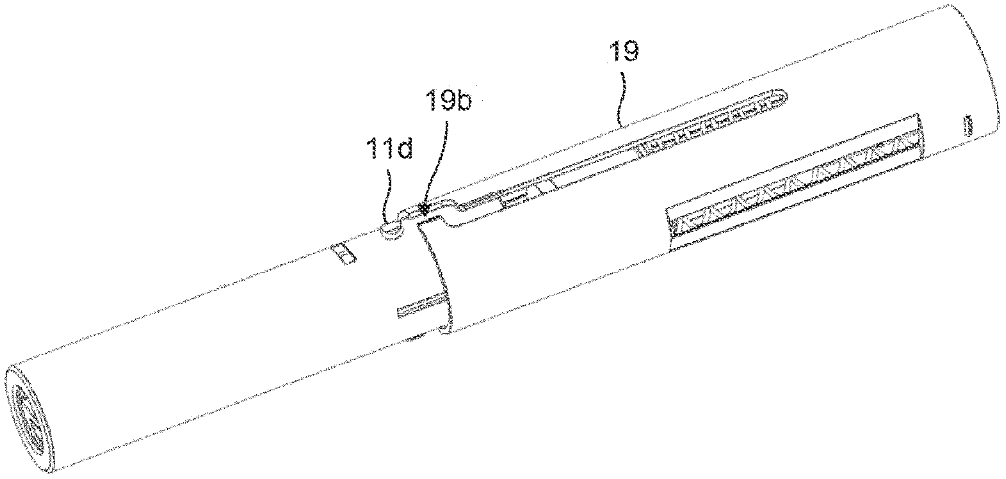
FIG. 5 shows the medicament delivery device without an outer rear body in the same situation as in FIG. 4.

FIG. 4 shows a step of attachment of the front assembly 3 with the rear assembly 5. The front assembly 3, with the syringe 15 arranged in the syringe holder 15 is moved into the front opening of the rear assembly 5. The pin 11*d* is aligned with the radial opening 7*b* in the front flange 7*a* of the outer rear body 7 when the front assembly 3 is brought into the rear assembly 5. The pin 11*d* can thereby run through the radial opening 7*a* and into the bayonet slot 19*b*. The front body 11 may be provided with a visual marker 11*e* for facilitating alignment of the front body 11 and the radial opening 7*b*. The pin 11*d* is first slid into the first axial portion of the bayonet slot 19*b*. The situation shown in FIG. 4 is also shown in FIG. 5, with the outer rear body 7 removed to better illustrate the orientation of the pin 11*d* relative to the bayonet slot 19*b*.

The next step during assembly of the medicament delivery device 1 is to rotate the front assembly 3 relative to the rear assembly 5 to move the pin 11*d* in the circumferential direction in the bayonet slot 19*b*. The pin 11*d* is thereby moved into the circumferential portion of the bayonet slot 19*b*. The front assembly 3 is thus axially locked relative to the rear assembly 5.

Figure 6:
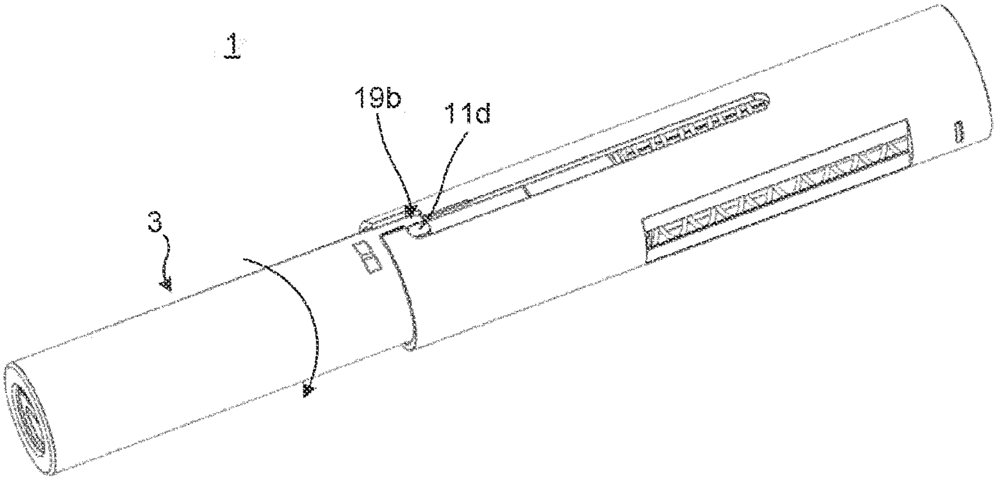
FIG. 6 shows the medicament delivery device without the outer rear body when the front assembly has been connected and locked to the rear assembly.

FIG. 6 shows the medicament delivery device 1 when the pin 11*d* has been received by the bayonet slot 19*b* and the pin 11*d* is arranged in the circumferential slot. The front assembly 3 has thereby been locked to the rear assembly 5.

Figure 7:
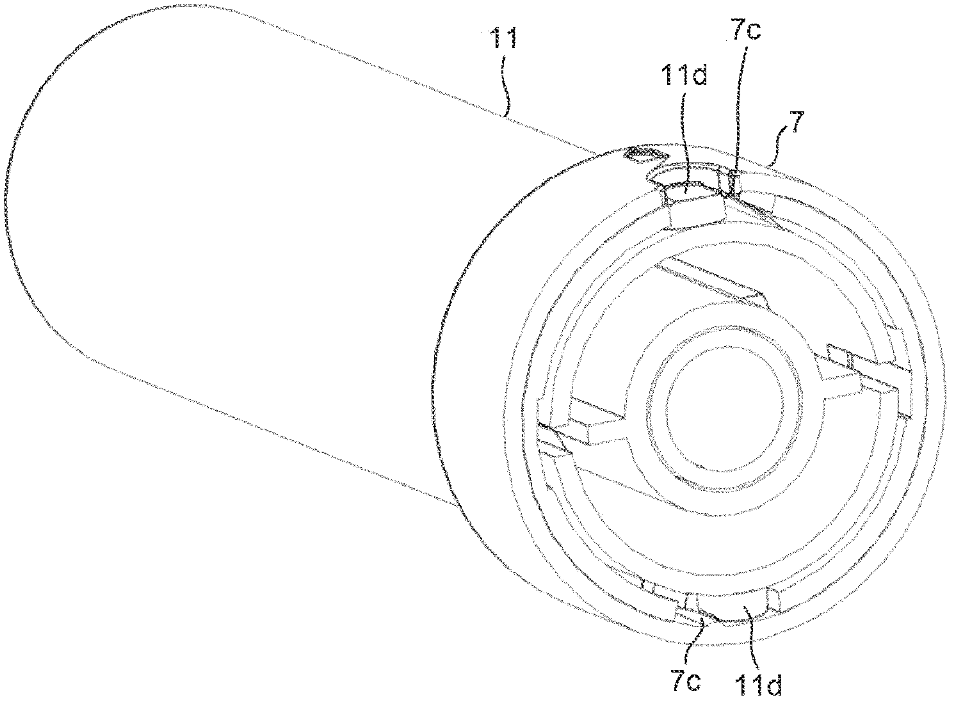
FIG. 7 is a perspective view of a cross-section of the medicament delivery device along lines A-A shown in FIG. 1.

FIG. 7 shows a cross-section along lines A-A of the medicament delivery device 1 in FIG. 1. The pin 11*d* is in the bayonet slot 19*b*, in particular the circumferential portion thereof. The axial rib 7*c* is arranged between the pin 11*d* and the first axial portion of the bayonet slot 19*b*, thereby restricting such rotation of the front assembly 3 relative to the rear assembly 5 which would release the front assembly 3 from its locked state with the rear assembly 5.

Figure 8:
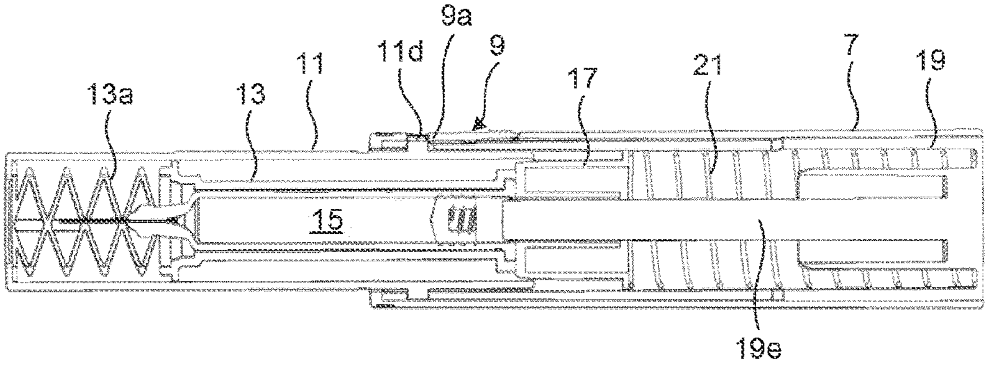
FIG. 8 is a longitudinal section of the medicament delivery device before medicament delivery has been initiated.

FIG. 8 shows a longitudinal section of the medicament delivery device 1 in the same state as shown in FIG. 1, i.e. when the medicament delivery device 1 is ready for use.

The plunger rod 19*e* of the rear body 19 extends in the forward direction through the syringe stop 17 and into the rear end of the syringe 15.

In the present example, the release button 9 has a see-saw structure. One end of the see-saw structure has a radially inwards extending structure 9*a*. The radially inwards extending structure 9*a* is arranged aligned with the axial slot 19*c*, rearwards of the pin 11*d* when the pin 11*d* is arranged in the bayonet slot 19*b*. The pin 11*d* is thereby prevented from moving rearwards in the axial slot 19*c*. The front body 11 is thus prevented from moving further into the rear assembly 5.

When medicament is to be delivered, the user holds the outer rear body 7 and pushes the medicament delivery device 1 towards the site of injection. By depressing a rear end of the release button 9, the radially inwards extending structure 9*a* is moved radially outwards. The pin 11*d* is thereby able to pass by the radially inwards extending structure 9*a* and move rearwards in the axial slot 19*c*.

Figure 9:
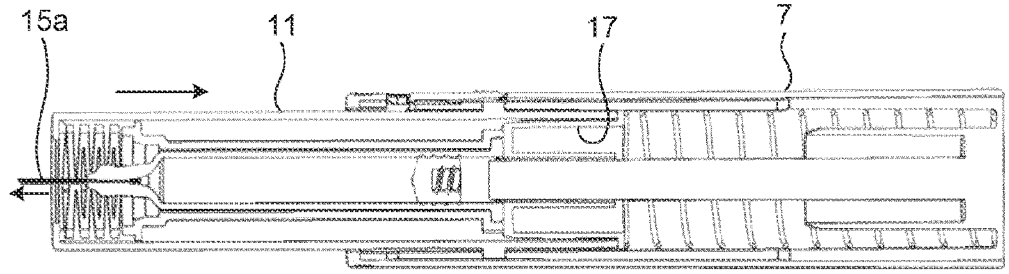
FIG. 9 is a longitudinal section of the medicament delivery device in a first phase of medicament delivery.

The rear resilient member 21 has a higher stiffness than the front resilient member 13*a*. As shown in FIG. 9, therefore, the front resilient member 13*a* is compressed before the rear resilient member 21. As a result, the syringe stop 17 is maintained in a fixed axial position inside the outer rear body 7 in the first stage of medicament delivery. The front body 11 is moved rearwards around the syringe stop 17, while the syringe stop 17 keeps the syringe 15 in a fixed axial position. The syringe 15 including the needle 15*a* is thus moved forward in the front body 11 and the needle 15*a* is eventually exposed at the front of the medicament delivery device 1. As a result, the needle 15*a* penetrates the site of injection.

Figure 10:
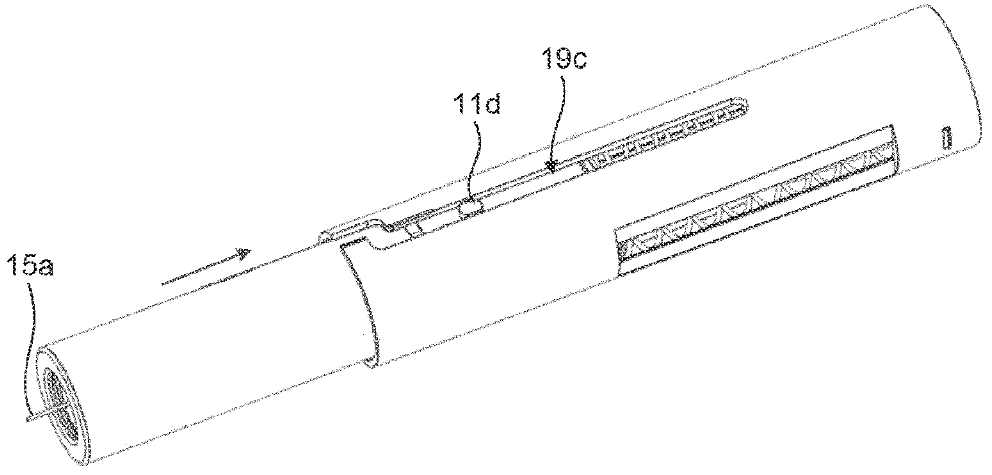
FIG. 10 is a perspective view of the medicament delivery device without the outer rear body in the same phase of medicament delivery as in FIG. 9.

FIG. 10 depicts the medicament delivery device 1 without the outer rear body 7 to show how the pin 11*d* moves rearwards along the axial slot 19*c* of the outer body 19 as the front body 11 is moved rearwards in the situation shown in FIG. 9.

Figure 11:
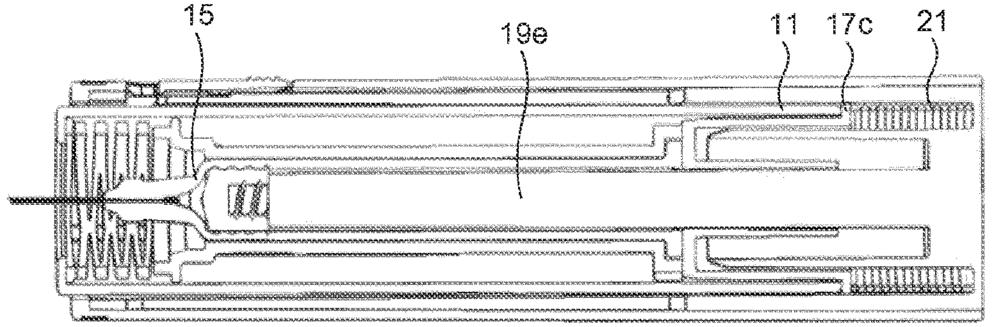
FIG. 11 is a longitudinal section of the medicament delivery device when the medicament delivery operation has been completed.

In FIG. 11, a state of the medicament delivery device 1 when full medicament delivery has been performed is shown. In this case, the user has maximally pushed the medicament delivery device 1 towards the site of injection. As the rear assembly 5 is further pushed towards the site of injection after the state of injection shown in FIG. 9, the rear end of the front body 11 reaches a flange surface 17*c* of the syringe stop 17, causing the forward-biased syringe stop 17 to move rearwards when the front body 11 is further moved into the rear body 19 and the front resilient member 13*a* has been fully compressed. The plunger rod 19*e* is thereby moved forward inside the syringe 15, causing medicament expulsion.

When the injection has been performed, the medicament delivery device 1 is removed from the site of injection and the medicament delivery device 1 obtains the state shown in FIG. 8. The user may now remove the used syringe by turning the rear assembly 5 in the opposite direction compared to the direction of rotation during assembly. Some force is required to overcome the force applied by the axial rib 7*a* onto the pin 11*d*. The pin 11*d* may be chamfered in both circumferential directions. This facilitates moving the pin 11*d* past the axial rib 7*a*. The front assembly 3 may then be pulled out from the rear assembly 5 and the used syringe can be removed from the front assembly 3 and discarded.

Figure 12:
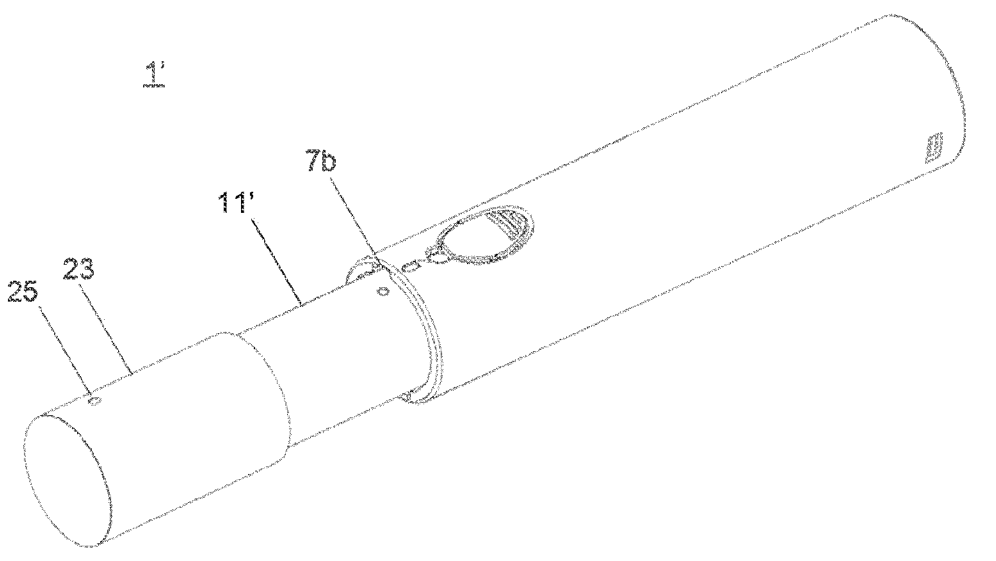
FIG. 12 is a perspective view of another example of a medicament delivery device.

FIG. 12 shows another example of a medicament delivery device 1'. The medicament delivery device 1' comprises a cap 23. The cap 23 can be fitted onto the front body 11'. The cap 23 can be removably attached to the front body 11'. The cap 23 has an opening configured to receive a front portion of the front body 11'.

The cap 23 has a first connection structure 25 configured to engage or mate with the front body 11'. The cap 23 can thereby be retained on the front body 11' until a user applying sufficient force pulls off the cap 23 for using the medicament delivery device 1'.

Figure 13:
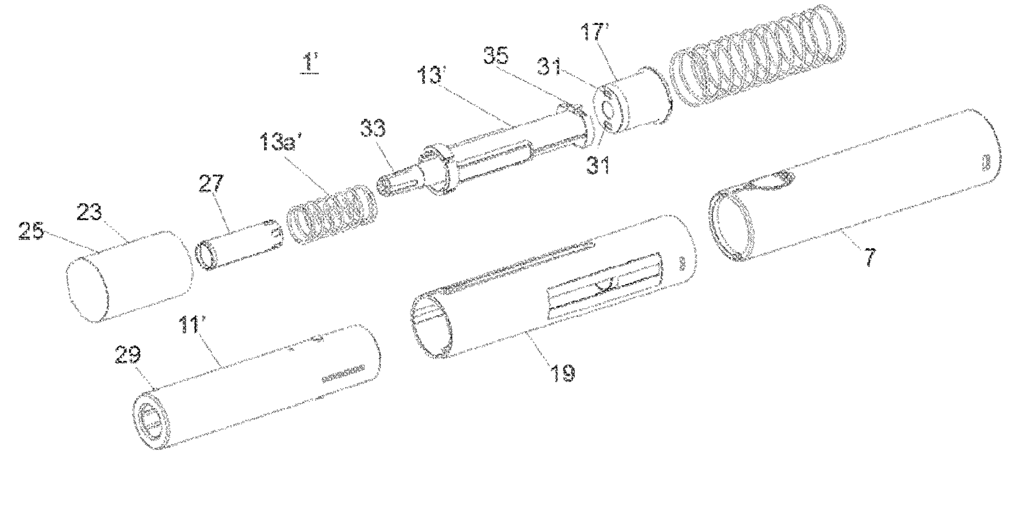
FIG. 13 is an exploded view of the medicament delivery device in FIG. 12.

FIG. 13 shows an exploded view of the medicament delivery device 1'. The medicament delivery device 1' is similar to the medicament delivery device 1. According to the example, the medicament delivery device 1' comprises a front resilient member 13*a*' that is a separate component from the syringe holder 13'. The front resilient member 13*a*' may be a spring, such as a coil spring. The front resilient member could alternatively be integral with the syringe holder like for the medicament delivery device 1.

The cap 23 comprises rigid needle shield (RNS) remover 27 arranged in a main body of the cap 23. The RNS remover 27 has gripping members configured to grip an RNS 33 arranged on the needle of the syringe. Thus, when the cap 23 is removed by a user, the RNS 33 is removed together with the cap 23.

The front body 11' has a second connection structure 29 configured to mate or engage with the first connection structure 25 of the cap 23.

The first connection structure 25 may be an opening, i.e. a radial opening and the second connection structure 29 may be a radial protrusion, such as a pin, extending radially outwards and configured to be received by the opening. The second connection structure 29 may be axially aligned with the radial opening 7*b* of the outer rear body 7, and configured to be received by the radial opening 7*b* when the front body 11' is moved further into the outer rear body 7 during a medicament delivery operation.

Alternatively, the first connection structure may be a radially inwards extending protrusion and the second connection structure may be an opening configured to receive the first connection structure.

The syringe holder 13' has a rear flange provided with rearwards extending radially flexible arms 35, each provided with a radially inwards extending protrusion (not shown in FIG. 13). The arms 35 are arranged opposite to each other.

The syringe stop 17' has axial openings 31 configured to receive the flexible arms 35.

Figure 14:
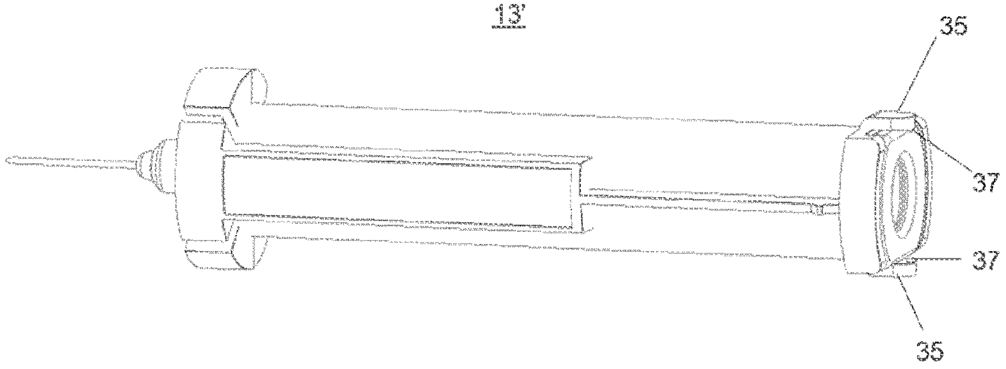
FIG. 14 shows a perspective view of the syringe holder of the medicament delivery device in FIG. 12.

FIG. 14 shows a perspective view of the syringe holder 13' with the syringe arranged inside, illustrating the radially inwards extending protrusions 37. The radially inwards extending protrusions 37 extend towards each other. The radially inwards extending protrusions 37 extend behind the rear side or end of the rear syringe flange to retain the syringe in the syringe holder 13'.

The present concept has mainly been described above with reference to a few examples. However, as is readily appreciated by a person skilled in the art, other embodiments than the ones disclosed above are equally possible within the scope of the present concept, as defined by the appended claims.

The invention claimed is:

1. A medicament delivery device comprising:

a front assembly;

a rear assembly; and a bayonet connection configured to attach the front assembly and the rear assembly;

wherein the front assembly has a front body and a syringe holder arranged in the front body, wherein the rear assembly has a rear body provided with a plunger rod, wherein the front body is configured to move axially relative to the rear body to enable the plunger rod to move forward inside the syringe holder, wherein the front body has a radial pin forming one part of the bayonet connection and the rear body has a bayonet slot forming another part of the bayonet connection, and wherein the pin is configured to run in the bayonet slot, wherein the radial pin is provided on an outer surface of the front body and the bayonet slot extends radially through the rear body, wherein the rear assembly further comprises an outer rear body configured to receive the rear body and a rear part of the front body, wherein the outer rear body has an axial rib provided on an inner surface of the outer rear body, the axial rib being configured to restrict movement of the pin in the bayonet slot to maintain the front body and the rear body in a locked state.

2. The medicament delivery device as claimed in claim 1, wherein the bayonet slot is configured to transition into an axial slot extending rearwards along the rear body, wherein the pin is configured to run in the axial slot to enable axial movement of the front body relative to the rear body when the front body and the rear body are locked by the bayonet connection.

3. The medicament delivery device as claimed in claim 2, wherein an axial length of the axial slot defines a stroke length of the front body.

4. The medicament delivery device as claimed in claim 1, wherein the outer rear body has a front flange provided with a radial opening aligned with a mouth of the bayonet slot, the radial opening being configured to receive the pin when the front assembly and rear assembly are assembled or disassembled with each other.

5. The medicament delivery device as claimed in claim 1, wherein the outer rear body has a release button which in a default position has a radially inwards extending structure configured to prevent axial movement of the pin on the front body rearwards in an axial slot of the bayonet slot, to thereby prevent the front body to move axially rearwards relative to the rear body, wherein the release button is configured to move the radially inwards extending structure radially outwards when the release button is depressed to enable the pin to run rearwards in the axial slot.

6. The medicament delivery device as claimed in claim 5, wherein the release button has a seesaw-structure with one end of the seesaw-structure being provided with the radially inwards extending structure.

7. The medicament delivery device as claimed in claim 1, wherein the rear body has an outer shell, and the plunger rod is arranged immovable relative to the outer shell, wherein the plunger rod extends in a forward direction inside the outer shell.

8. The medicament delivery device as claimed in claim 1, comprising a front resilient member arranged in the front body and configured to bias the syringe holder towards a rear end of the front body.

9. The medicament delivery device as claimed in claim 1, comprising an axially movable syringe stop arranged in the rear body concentrically with the plunger rod, wherein the syringe stop has radial protrusions and the rear body comprises axial slots in which the radial protrusions are configured to run to guide axial movement of the syringe stop, and a rear resilient member configured to bias the syringe stop towards a front end of the rear body.

10. The medicament delivery device as claimed in claim 9, wherein the syringe stop is configured to bear against a rear end of the syringe holder.

11. The medicament delivery device as claimed in claim 9, wherein the rear resilient member has a higher stiffness than a front resilient member.

12. The medicament delivery device as claimed in claim 1, wherein the front body is a needle cover.

13. A medicament delivery device comprising:

a front assembly;

a rear assembly configured to be attached to the front assembly, wherein the rear assembly has a rear body provided with a plunger rod;

a bayonet connection comprising a pin extending radially outward from the front assembly and a bayonet slot located on the rear assembly, and an outer rear body in sliding engagement with the rear body, where an inside surface of the outer rear body comprises a longitudinal axial rib that defines a detent that prevents relative rotation of the front body relative to the rear body;

wherein the front assembly has a front body and a syringe holder arranged in the front body, wherein the front body is configured to move axially relative to the rear body to enable the plunger rod to move forward inside the syringe holder, wherein the front assembly and the rear assembly are configured to be attached by means of the bayonet connection.

14. The medicament delivery device of claim 13, wherein the pin slides within the bayonet slot along a path when the front body moves axially relative to the rear body.

15. The medicament delivery device of claim 14, wherein the path comprises an axial slot that defines a stroke length of the front body.

16. The medicament delivery device of claim 13 further comprising a release button having a seesaw-structure such that a radially outward movement of a proximal end of the release button disengages a portion of the seesaw-structure from the pin to allow the front body to move distally relative to the rear body.

* * * * *